US009718743B2

(12) United States Patent
Liu et al.

(10) Patent No.: US 9,718,743 B2
(45) Date of Patent: Aug. 1, 2017

(54) METHOD FOR PREPARING A LIGHT OLEFIN USING AN OXYGEN-CONTAINING COMPOUND, AND DEVICE FOR USE THEREOF

(71) Applicant: DALIAN INSTITUTE OF CHEMICAL PHYSICS, CHINESE ACADEMY OF SCIENCES, Dalian (CN)

(72) Inventors: Zhongmin Liu, Dalian (CN); Mao Ye, Dalian (CN); Tao Zhang, Dalian (CN); Changqing He, Dalian (CN); Xiangao Wang, Dalian (CN); Yinfeng Zhao, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

(21) Appl. No.: 15/100,834

(22) PCT Filed: Dec. 3, 2013

(86) PCT No.: PCT/CN2013/088388
§ 371 (c)(1),
(2) Date: Jun. 1, 2016

(87) PCT Pub. No.: WO2015/081484
PCT Pub. Date: Jun. 11, 2015

(65) Prior Publication Data
US 2016/0304412 A1 Oct. 20, 2016

(51) Int. Cl.
*C07C 1/20* (2006.01)
*C07C 1/207* (2006.01)
(Continued)

(52) U.S. Cl.
CPC ............... *C07C 1/20* (2013.01); *B01J 8/1827* (2013.01); *B01J 8/1836* (2013.01); *B01J 8/1872* (2013.01);
(Continued)

(58) Field of Classification Search
CPC C07C 1/20; C07C 1/207; C07C 1/213; C07C 1/24; C07C 1/247; B01J 38/30; B01J 38/34
(Continued)

(56) References Cited

U.S. PATENT DOCUMENTS 6,166,282 A    12/2000    Miller
2005/0101816 A1    5/2005    Xu et al.
(Continued)

FOREIGN PATENT DOCUMENTS

CN    101239870 A    8/2008
CN    101367694 A    2/2009
(Continued)

OTHER PUBLICATIONS

Written Opinion issued on Jul. 30, 2014 for PCT Application No. PCT/CN2013/088388.
(Continued)

*Primary Examiner* — Thuan D Dang
(74) *Attorney, Agent, or Firm* — Enshan Hong; VLP Law Group LLP (57) ABSTRACT

A method for preparing a light olefin using an oxygen-containing compound, and a device for use thereof, more specifically, taking methanol and/or dimethyl ether as main starting materials, using a multi-stage (n≥2) dense phase fluidized bed reactor and a multi-stage (m≥2) catalyst regenerator, which solves the problem in the prior art of the
(Continued)

uniformity of catalyst carbon deposition and the carbon content being difficult to control and the light olefin selectivity being low.

20 Claims, 5 Drawing Sheets (51) Int. Cl.
<table>
<tr><td>C07C 1/213</td><td>(2006.01)</td></tr>
<tr><td>C07C 1/24</td><td>(2006.01)</td></tr>
<tr><td>C07C 1/247</td><td>(2006.01)</td></tr>
<tr><td>B01J 38/30</td><td>(2006.01)</td></tr>
<tr><td>B01J 38/34</td><td>(2006.01)</td></tr>
<tr><td>B01J 8/26</td><td>(2006.01)</td></tr>
<tr><td>B01J 8/18</td><td>(2006.01)</td></tr>
<tr><td>B01J 29/85</td><td>(2006.01)</td></tr>
<tr><td>B01J 29/90</td><td>(2006.01)</td></tr>
<tr><td>B01J 38/06</td><td>(2006.01)</td></tr>
<tr><td>B01J 38/12</td><td>(2006.01)</td></tr>
</table>

(52) U.S. Cl.
CPC ............... *B01J 8/26* (2013.01); *B01J 29/85* (2013.01); *B01J 29/90* (2013.01); *B01J 38/06* (2013.01); *B01J 38/12* (2013.01); *B01J 2208/00902* (2013.01); *C07C 2529/85* (2013.01); *Y02P 20/584* (2015.11); *Y02P 30/42* (2015.11)

(58) Field of Classification Search
USPC ............................... 585/639, 640; 502/41, 43
See application file for complete search history.

(56) References Cited

U.S. PATENT DOCUMENTS

2006/0135834 A1* 6/2006 Xu .......................... C07C 1/20
 585/639
2010/0331596 A1 12/2010 Xie et al.
2011/0152479 A1 6/2011 Nesterenko

FOREIGN PATENT DOCUMENTS

<table>
<tr><td>CN</td><td>101367700 A</td><td>2/2009</td></tr>
<tr><td>CN</td><td>101327445 B</td><td>6/2010</td></tr>
<tr><td>CN</td><td>102464535 A</td><td>5/2012</td></tr>
<tr><td>CN</td><td>101402538 B</td><td>1/2013</td></tr>
<tr><td>CN</td><td>103193574 A</td><td>7/2013</td></tr>
<tr><td>CN</td><td>102276406 B</td><td>7/2014</td></tr>
<tr><td>CN</td><td>102875291 B</td><td>11/2014</td></tr>
<tr><td>CN</td><td>102875289 B</td><td>12/2014</td></tr>
<tr><td>CN</td><td>102875296 B</td><td>1/2015</td></tr>
<tr><td>EA</td><td>200801961 A1</td><td>4/2009</td></tr>
<tr><td>WO</td><td>2012152258 A1</td><td>5/2012</td></tr>
</table>

OTHER PUBLICATIONS

International Search Report mailed on Jul. 30, 2014 for PCT Application No. PCT/CN2013/088388.
Office Action issued Feb. 1, 2016 in counterpart Chinese Patent Application No. 201310643502.1.
Search Report for related Singapore Application No. 11201604429V issued by Intellectual Property Office of Singapore on Sep. 1, 2016.
Search Report for related Australian Application No. 2013407180 issued by Australian Intellectual Property Office on Nov. 1, 2016.
Office Action for related Japan Application No. 2016-535-725 issued by Japan Patent Office on Apr. 14, 2017.
Office Action for related Russian Application No. 2016126180 completed by Russian Intellectual Property Office on Apr. 28, 2017.

* cited by examiner

C-C section

Figure 4

Front view    Left sectional view

D–D section

Figure 5

METHOD FOR PREPARING A LIGHT OLEFIN USING AN OXYGEN-CONTAINING COMPOUND, AND DEVICE FOR USE THEREOF

RELATED APPLICATIONS

This is a U.S. national stage of international application No. PCT/CN2013/088388 filed on Dec. 3, 2013.

TECHNICAL FIELD

The present disclosure relates to a method for preparing a light olefin using an oxygen-containing compound, and a device for use thereof.

BACKGROUND

Light olefins, i.e. ethylene and propylene, are two important kinds of basic chemical raw materials, and the demand thereof is increasing. Generally, ethylene and propylene are produced via a petroleum scheme. However, the costs for producing ethylene and propylene from petroleum resources are increasing due to limited supply and relatively high price of petroleum resources. In recent years, techniques for preparing ethylene and propylene by converting substituent raw materials have been greatly developed. More and more attentions have been paid to the process of methanol-to-olefins (MTO), and the production scale of megatonnage has been achieved. As the world economy develops, the demand for light olefins, particularly propylene, is increasing day by day. It is reported as the analysis of CMAI Corporation that the demand for ethylene will increase at an average rate of 4.3% per year and the demand for propylene will increase at an average rate of 0.4% per year until 2016. Due to high-speed increase of the economy in China, all of the annual increase rates of the demand for ethylene and propylene in China exceed the average level of the world.

In early 1980s, UCC Corporation successfully developed SAPO series molecular sieves. Among others, SAPO-34 molecular sieve catalyst exhibits excellent catalytic performance when it is used in MTO reaction, and has very high selectivity for light olefins and very high activity. However, after the catalyst has been used for a period of time, the activity is lost due to carbon deposition. A remarkable induction period is present in the use of the SAPO-34 molecular sieve catalyst. In the induction period, the selectivity for olefins is relatively low and the selectivity for alkanes is relatively high. As the reaction time increases, the selectivity for light olefins gradually increases. After the induction period, the catalyst maintains high selectivity and high activity in a certain period of time. With further prolong of the time, however, the activity of the catalyst rapidly decreases.

U.S. Pat. No. 6,166,282 discloses a technique and a reactor for converting methanol to light olefins, which use a fast fluidized bed reactor, wherein after the completion of a reaction in a dense phase reaction zone having a relatively low gas speed, the gas phase rises to a fast separation zone having an inner diameter which rapidly becomes smaller, and most of the entrained catalyst is preliminarily separated using a special gas-solid separation apparatus. Since the product gas and the catalyst are rapidly separated after reaction, a secondary reaction is effectively prevented. Upon analog computation, the inner diameter of the fast fluidized bed reactor and the catalyst inventory required are both greatly reduced, compared to the conventional bubbling fluidized bed reactors. However, the carbon based yields of light olefins in this method are all typically about 77%, and there are problems concerning relatively low yields of light olefins.

CN101402538B discloses a method for increasing the yield of light olefins. This method provides a second reaction zone on the upper part of a first reaction zone for converting methanol to light olefins, and the diameter of the second reaction zone is greater than that of the first reaction zone to increase the residence time of the product gas from the outlet of the first reaction zone in the second reaction zone, such that the unreacted methanol, the generated dimethyl ether, and hydrocarbons having 4 or more carbons continue to react so as to achieve the object of increasing the yield of light olefins. This method may increase the yield of light olefins to some extent. However, since the catalyst come out from the first reaction zone has already carried a relatively great amount of deposited carbon and relatively high catalyst activity is required to crack hydrocarbons having 4 or more carbons, the conversion efficiencies of hydrocarbons having 4 or more carbons in the second reaction zone in this method are still relatively low, leading to a lower yield of light olefins.

CN102276406A discloses a method for increasing the production of propylene. This technique provides three reaction zones, wherein a first fast bed reaction zone is used for converting methanol to olefins, and a lift pipe reaction zone and a second fast bed reaction zone are connected in series to convert ethylene, hydrocarbons having 4 or more carbons, and unreacted methanol or dimethyl ether. In this patent application, the residence times of substances, such as hydrocarbons having 4 or more carbons, etc., in the lift pipe reaction zone and in the second fast bed reaction zone are relatively short and the conversion efficiencies are relatively low, such that the yield of propylene is relatively low.

CN102875289A discloses a fluidized bed reaction device with a lift pipe reactor arranged therein, which is used for increasing the yield of light olefins. A first raw material is passed into a fluidized bed reaction zone and is brought into contact with a catalyst to generate a product comprising light olefins, and at the meanwhile a spent catalyst is formed; a part of the spent catalyst is passed into a regenerator for regeneration to form a regenerated catalyst, and the other part of the spent catalyst is passed into a lift pipe with an outlet end located inside the reaction zone and is brought into contact with a second raw material so as to lift the spent catalyst into the reaction zone; and the regenerated catalyst is returned to the reaction zone of the fluidized bed reactor. Since the reaction device disclosed in this patent application does not comprise a stripping portion, the spent catalyst will be passed into the regenerator with carrying a part of the product gas, which is combusted with oxygen to reduce the yield of light olefins.

The technique for preparing olefins from methanol disclosed in CN102875296A provides three reaction zones, which are a fast bed, a downer, and a lift pipe. Since the catalyst is circulated among the regenerator, the fast bed, the lift pipe, and the downer, the flow direction is extremely complicated, the distribution and the control of the flow rate are extremely difficult, and the activity of catalyst greatly varies.

As well known in the art, the selectivity for light olefins is closely associated with the amount of carbon deposition on the catalyst. A certain amount of carbon deposition on SAPO-34 catalyst is needed to ensure a high selectivity for light olefins. Main reactors used in current MTO process are fluidized beds. The fluidized bed is close to a perfect mixing flow reactor, which has a wide distribution of carbon deposition on catalyst and is not advantageous for increasing the selectivity for light olefins. Since the catalyst-to-alcohol ratio is very small and the coke yield is relatively low in the MTO process, in order to achieve a lager and controllable catalyst circulation volume, it is required to control the amount of carbon deposition and the uniformity of carbon content on the catalyst to a certain level in the regeneration zone, thereby achieving the object of controlling the amount of carbon deposition and the uniformity of carbon content on the catalyst in the reaction zone. Therefore, it is a key technique in the MTO process to control the amount of carbon deposition and the uniformity of carbon content of the catalyst in the reaction zone to a certain level.

In order to solve the problems described above, some researchers propose the techniques, such as providing an upper and a lower reaction zones in a fluidized bed, two fluidized beds connected in series, and a fluidized bed, a lift pipe, and a downer connected in series, etc. These preliminarily disclose methods for controlling the amount of carbon deposition and the uniformity of carbon content of the catalyst, and certain advantageous effects have been obtained. However, the complexity and the difficulty for controlling the MTO process are increased at the meanwhile. The present disclosure proposes a solution in which a plurality of secondary reaction zones (regeneration zones) are formed by providing inner members in a dense phase fluidized bed, to solve the problem of controlling the amount of carbon deposition and the uniformity of carbon content of the catalyst so as to increase the selectivity for light olefins.

SUMMARY OF THE DISCLOSURE

The technical problem to be solved by the present disclosure is the problem that the selectivity for light olefins is not high in the prior art, and the object is to provide a new method for increasing the selectivity for light olefins. This method is used in the production of light olefins, and has the advantages of good uniformity of carbon deposition on catalyst, relatively high yield of light olefins, and good economical efficiency of the production process of light olefins.

In order to achieve the above object, in one aspect, the present disclosure provides a method for preparing a light olefin using an oxygen-containing compound, comprising the following steps:

step a) in which a raw material comprising the oxygen-containing compound is introduced in parallel from n feeding branch lines into $1^{st}$ to $n^{th}$ secondary reaction zones in a dense phase fluidized bed reactor, and is brought into contact with a catalyst to generate a light olefin product-containing stream and a spent catalyst, wherein said catalyst is sequentially passed through $1^{st}$ to $n^{th}$ secondary reaction zones, with the carbon content thereof increasing gradually, and wherein said dense phase fluidized bed reactor is divided by a material flow controller into n secondary reaction zones;

step b) in which the light olefin product-containing stream flowed out from the $1^{st}$ to $n^{th}$ secondary reaction zones is separated from the spent catalyst that it carries; said light olefin product-containing stream is passed into a product separation section, and after separation and purification, a light olefin product is obtained; the isolated spent catalyst is passed into the $n^{th}$ secondary reaction zone; and step c) in which the spent catalyst flowed out from the $n^{th}$ secondary reaction zone, after being stripped and lifted, is passed into a dense phase fluidized bed regenerator for regeneration; said spent catalyst is sequentially passed through $1^{st}$ to $m^{th}$ secondary regeneration zones; a regeneration medium is introduced in parallel from m feeding branch lines of regeneration zone into the $1^{st}$ to $m^{th}$ secondary regeneration zones; the spent catalyst is brought into contact with the regeneration medium, with the carbon content thereof decreasing gradually; after the completion of the regeneration, the catalyst is returned back to the $1^{st}$ secondary reaction zone via stripping and lifting; wherein the dense phase fluidized bed regenerator is divided by a material flow controller into m secondary regeneration zones; wherein n≥2 and m≥2, more preferably 8≥n≥3 and 8≥m≥3.

In a preferred embodiment, in the dense phase fluidized bed reactor, the apparent linear velocity of gas in the material flow controller is less than or equals to the minimum fluidizing velocity of the catalyst.

In a preferred embodiment, in the dense phase fluidized bed regenerator, the apparent linear velocity of gas in the material flow controller is less than or equals to the minimum fluidizing velocity of the catalyst.

In a preferred embodiment, the catalyst comprises SAPO-34 molecular sieve.

In a preferred embodiment, the reaction conditions of the reaction zone in the dense phase fluidized bed are as follows: the apparent linear velocity of gas is 0.1-1.5 m/s, reaction temperature is 400-550° C., the bed density is 200-1200 kg/m$^3$.

In a preferred embodiment, the average carbon deposition amount of the catalyst is increased sequentially in the $1^{st}$ to $n^{th}$ secondary reaction zones of the dense phase fluidized bed, wherein the average carbon deposition amount of the catalyst in the $1^{st}$ secondary reaction zone is 0.5-3 wt %, the average carbon deposition amount of the catalyst in the $n^{th}$ secondary reaction zone is 7-10 wt %.

In a preferred embodiment, the reaction conditions in the dense phase fluidized bed regeneration zone are as follows: the apparent linear velocity of gas is 0.1-1.5 m/s, the regeneration temperature is 500-700° C., and the bed density is 200-1200 kg/m$^3$.

In a preferred embodiment, the average carbon deposition amount of the catalyst is decreased sequentially from the $1^{st}$ to $m^{th}$ secondary regeneration zones of the dense phase fluidized bed regeneration zone, wherein the average carbon deposition amount of the catalyst in the $1^{st}$ secondary regeneration zone is 3-10 wt %, and the average carbon deposition amount of the catalyst in the $m^{th}$ secondary regeneration zone is 0-3 wt %.

In a preferred embodiment, the oxygen-containing compound is methanol and/or dimethyl ether; the light olefin is any one of ethylene, propylene or butylenes, or a mixture thereof; and the regeneration medium is any one of air, oxygen-deficient air or water vapor, or a mixture thereof.

In another aspect, the present disclosure provides a dense phase fluidized bed reactor for carrying out the above method, said dense phase fluidized bed reactor comprising a reaction zone, a gas-solid separation zone, and a stripping zone, wherein said reaction zone is divided by a material flow controller into n secondary reaction zones, wherein n≥2.

In another aspect, the present disclosure provides a dense phase fluidized bed regenerator for carrying out the above method, said dense phase fluidized bed regenerator comprising a regeneration zone, a gas-solid separation zone, and a stripping zone, wherein said regeneration zone is divided by a material flow controller into m secondary regeneration zones, wherein m≥2.

The advantageous effects of the present disclosure include, but are not limited to, the following aspects: (1) the dense phase fluidized bed has a relatively high bed density, a relatively low catalyst velocity, and a low abrasion; (2) the gas velocity in the material downward flow pipe of the material flow controller is less than or equals to the minimal fluidization velocity of the catalyst and the catalyst is in a dense phase packing state, such that a unidirectional dense phase conveying stream of the catalyst is formed, the backmixing of catalyst between adjacent secondary reaction zones (or adjacent secondary regeneration zones) is prevented, and the distribution of residence time is narrow; (3) the heat extraction member in the material flow controller has an effect of controlling the temperature of the reaction zone; (4) the reaction zone is divided into n secondary reaction zones by the material flow controller and the catalyst sequentially passes through the $1^{st}$ secondary reaction zone to the $n^{th}$ secondary reaction zone, such that the distribution of residence time is narrow and the uniformity of carbon content of the spent catalyst is greatly increased; (5) the regeneration zone is divided into m secondary regeneration zones by the material flow controller and the catalyst sequentially passes through the $1^{st}$ secondary regeneration zone to the $m^{th}$ secondary regeneration zone, such that the distribution of residence time is narrow and the uniformity of carbon content of the regenerated catalyst is greatly increased; (6) relatively precise control of carbon content of the regenerated catalyst and the spent catalyst is achieved, the distribution of carbon content is relatively uniform, the selectivity for light olefins is increased, and the carbon content may be regulated as needed to optimize the ratio of propylene/ethylene; (7) since the distribution of carbon content of the catalyst is relatively uniform, the catalyst inventory required in the reaction zone decreases; (8) the configuration of a plurality of secondary reaction zones facilitates the achievement of large-scale reactors.

1: reactor feed line; 1-1: feeding branch line of $1^{st}$ secondary reaction zone; 1-2: feeding branch line of $2^{nd}$ secondary reaction zone; 1-3: feeding branch line of $3^{rd}$ secondary reaction zone; 1-4: feeding branch line of $4^{th}$ secondary reaction zone; 2: dense phase fluidized bed reactor; 2-1: $1^{st}$ secondary reaction zone; 2-2: $2^{nd}$ secondary reaction zone; 2-3: $3^{rd}$ secondary reaction zone; 2-4: $4^{th}$ secondary reaction zone; 3: cyclone separator; 4: product material line; 5: stripper; 6: water vapor line; 7: lift pipe; 8: lifting gas line; 9: regenerator feed line; 9-1: feeding branch line of $1^{st}$ secondary regeneration zone; 9-2: feeding branch line of $2^{nd}$ secondary regeneration zone; 9-3: feeding branch line of $3^{rd}$ secondary regeneration zone; 9-4: feeding branch line of $4^{th}$ secondary regeneration zone; 10: dense phase fluidized bed regenerator; 10-1: $1^{st}$ secondary regeneration zone; 10-2: $2^{nd}$ secondary regeneration zone; 10-3: $3^{rd}$ secondary regeneration zone; 10-4: $4^{th}$ secondary regeneration zone; 11: cyclone separator; 12: exhaust gas line; 13: stripper; 14: water vapor line; 15: lift pipe; 16: lifting gas line; 17: material flow controller; 18: material overflow port; 19: partition plate; 20: orifice; 21: material downward flow pipe; 22: bottom baffle; 23: heat extraction member.

DESCRIPTION OF THE PREFERRED EMBODIMENTS

In order to increase the selectivity for light olefins in the process of preparation of a light olefin using an oxygen-containing compound, the present disclosure provides a method for preparing a light olefin using an oxygen-containing compound, comprising the following steps:

a) a step in which a raw material comprising the oxygen-containing compound is introduced in parallel from n feeding branch lines into $1^{st}$ to $n^{th}$ secondary reaction zones in a dense phase fluidized bed reactor, and is brought into contact with a catalyst to generate a light olefin product-containing stream and a spent catalyst, wherein said catalyst is sequentially passed through $1^{st}$ to $n^{th}$ secondary reaction zones, with the carbon content thereof increasing gradually, and wherein said dense phase fluidized bed reactor is divided by a material flow controller into n secondary reaction zones;

b) a step in which the light olefin product-containing stream flowed out from the $1^{st}$ to $n^{th}$ secondary reaction zones is separated from the spent catalyst that it carries; said light olefin product-containing stream is passed into a product separation section, and after separation and purification, a light olefin product is obtained; the isolated spent catalyst is passed into the $n^{th}$ secondary reaction zone; and c) a step in which the spent catalyst flowed out from the $n^{th}$ secondary reaction zone, after being stripped and lifted, is passed into a dense phase fluidized bed regenerator for regeneration; said spent catalyst is sequentially passed through $1^{st}$ to $m^{th}$ secondary regeneration zones; a regeneration medium is introduced in parallel from m feeding branch lines of regeneration zone into the $1^{st}$ to $m^{th}$ secondary regeneration zones; the spent catalyst is brought into contact with the regeneration medium, with the carbon content thereof decreasing gradually; after the completion of the regeneration, the catalyst is returned back to the $1^{st}$ secondary reaction zone via stripping and lifting; wherein the dense phase fluidized bed regenerator is divided by a material flow controller into m secondary regeneration zones.

Wherein n≥2, preferably 8≥n≥3; m≥2, preferably 8≥m≥3.

Preferably, in the dense phase fluidized bed reactor, the apparent linear velocity of gas in the material flow controller is less than or equals to the minimum fluidizing velocity of the catalyst.

Preferably, in the dense phase fluidized bed regenerator, the apparent linear velocity of gas in the material flow controller is less than or equals to the minimum fluidizing velocity of the catalyst.

Preferably, the catalyst comprises SAPO-34 molecular sieve.

Preferably, the reaction conditions of the reaction zone in the dense phase fluidized bed are as follows: the apparent linear velocity of gas is 0.1-1.5 m/s, reaction temperature is 400-550° C., the bed density is 200-1200 kg/m$^3$; the average carbon deposition amount of the catalyst in the $1^{st}$ secondary reaction zone is 0.5-3 wt %, and the average carbon deposition amount of the catalyst in the $n^{th}$ secondary reaction zone is 7-10 wt %.

Preferably, the reaction conditions in the dense phase fluidized bed regeneration zone are as follows: the apparent linear velocity of gas is 0.1-1.5 m/s, the regeneration temperature is 500-700° C., and the bed density is 200-1200 kg/m$^3$; the average carbon deposition amount of the catalyst is decreased sequentially from the $1^{st}$ to $m^{th}$ secondary regeneration zones, the average carbon deposition amount of the catalyst in the $1^{st}$ secondary regeneration zone is 3-10 wt %, and the average carbon deposition amount of the catalyst in the $m^{th}$ secondary regeneration zone is 0-3 wt %.

Preferably, the oxygen-containing compound is methanol and/or dimethyl ether; the light olefin is any one of ethylene, propylene or butylene, or a mixture thereof; the regeneration medium is any one of air, oxygen-deficient air or water vapor, or a mixture thereof.

The technical solution provided in the present disclosure may further comprises:

(1) providing a dense phase fluidized bed reactor, comprising a reaction zone, a gas-solid separation zone, and a stripping zone, the reaction zone being divided by a material flow controller into n secondary reaction zones, wherein n≥2;

(2) providing a dense phase fluidized bed regenerator, comprising a regeneration zone, a gas-solid separation zone, and a stripping zone, the regeneration zone being divided by a material flow controller into m secondary regeneration zones, wherein m≥2.

Preferably, the raw material comprising an oxygen-containing compound is introduced into the dense phase fluidized bed reactor and is brought into contact with regenerated catalyst, resulting in a light olefin-containing product and a carbon-containing spent catalyst, meanwhile, the regenerated catalyst is sequentially passed through $1^{st}$ to $n^{th}$ secondary reaction zones, with the carbon content thereof increasing gradually.

Preferably, via stripping and lifting, the spent catalyst flowing out from the $n^{th}$ secondary reaction zone is passed into the dense phase fluidized bed regenerator for regeneration, the spent catalyst is sequentially passed through $1^{st}$ to $m^{th}$ secondary regeneration zone, and is brought into contact with the regeneration medium, with the carbon content thereof gradually decreasing, and then the catalyst is returned back to $1^{st}$ secondary reaction zone via stripping and lifting.

Preferably, the stream of the light olefin product is passed into separation section after separation with spent catalyst, and the isolated spent catalyst is passed into $n^{th}$ secondary reaction zone.

Figure 1:
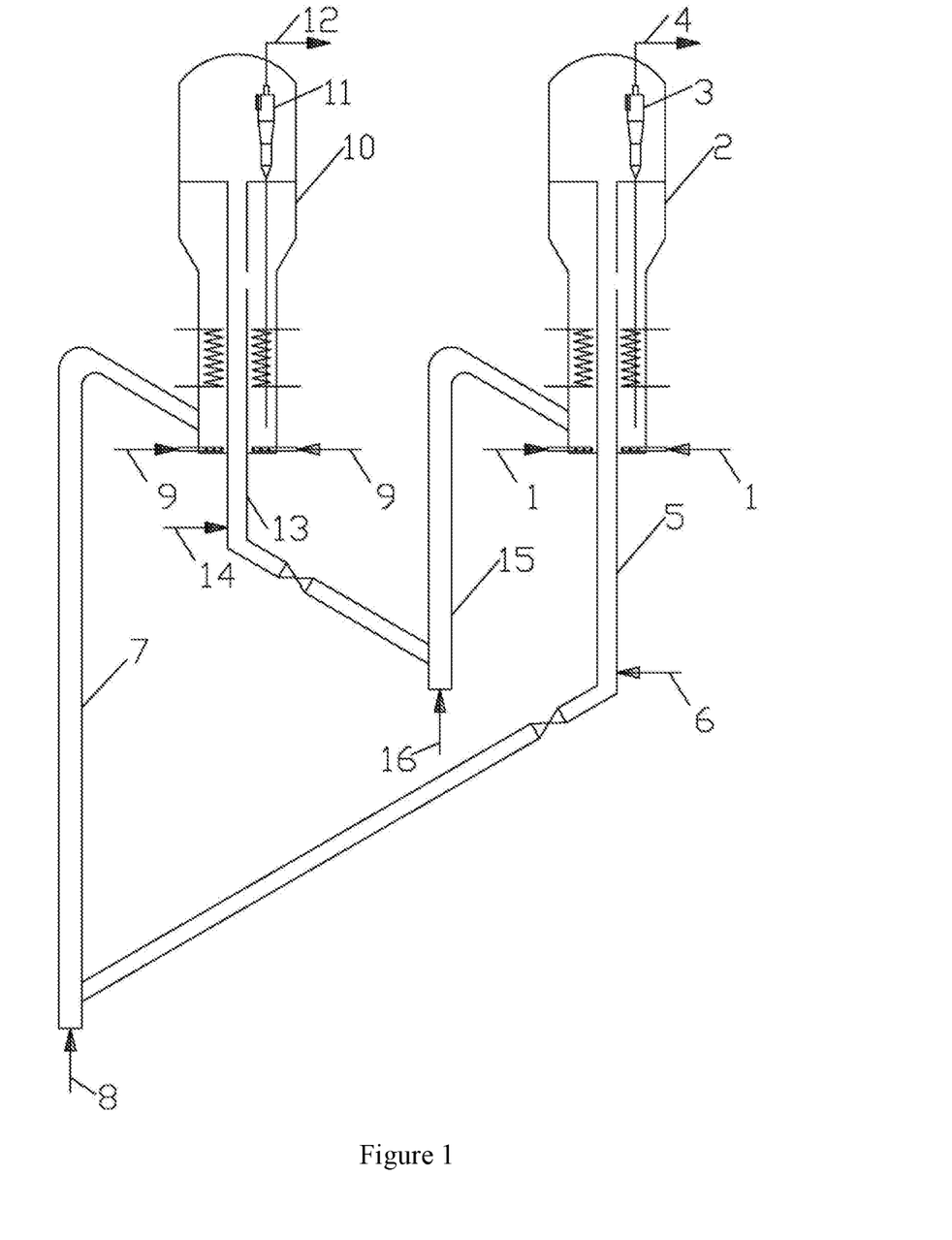
FIG. 1 is a schematic flow chart of the method in the present disclosure.

In a specific embodiment, the schematic flow chart for preparing a light olefin using a oxygen-containing compound in the present disclosure is as shown in FIG. 1. The raw material comprising the oxygen-containing compound is introduced from reactor feed line (1) and breach lines (1-1, . . . , 1-n) thereof in parallel into secondary reaction zones (2-1, . . . , 2-n) in the dense phase fluidized bed reactor (2), and is brought into contact with a catalyst comprising SAPO-34 molecular sieve, to generate a gas phase product stream and a spent catalyst. The gas phase product stream and the entrained spent catalyst are passed into a cyclone separator (3), wherein the gas phase product stream flows through the outlet of the cyclone separator and the product material line (4) and enters into the subsequent separation section, the entrained spent catalyst is passed into $n^{th}$ secondary reaction zone (2-n) via the dipleg of the cyclone separator; the regenerated catalyst from the dense phase fluidized bed regenerator (10) is passed into the dense phase fluidized bed reactor (2) via a stripper (13) and a lift pipe (15), wherein the bottom of the stripper (13) is connected to a water vapor line (14), and the bottom of the lift pipe (15) is connected to a lifting gas line (16); the regenerated catalyst is sequentially passed through $1^{st}$ to $n^{th}$ secondary reaction zones (2-1, . . . , 2-n) in the dense phase fluidized bed reactor (2), and forms spent catalyst after carbon deposition; the regeneration medium is introduced from regenerator feed line (9) and branch lines (9-1, . . . , 9-m) thereof into secondary regeneration zones (10-1, . . . , 10-m) in the dense phase fluidized bed regenerator (10), and is brought into contact with the spent catalyst, to generate exhaust gas and regenerated catalyst after charking, and then the exhaust gas and the entrained regenerated catalyst are passed into a cyclone separator (11), from which, the exhaust gas is passed into a tail gas processing section through the outlet of the cyclone separator and exhaust gas line (12), and is emitted after processing, and the entrained regenerated catalyst is passed into $m^{th}$ secondary regeneration zone (10-m) via the dipleg of the cyclone separator. The spent catalyst from the dense phase fluidized bed reactor (2) is passed into the dense phase fluidized bed regenerator (10) via a stripper (5) and a lift pipe (7), wherein the bottom of the stripper (5) is connected to a water vapor line (6), and the bottom of the lift pipe (7) is connected to a lifting gas line (8). In the dense phase fluidized bed regenerator (10), the spent catalyst is sequentially passed through $1^{st}$ to $m^{th}$ secondary regeneration zones (10-1, . . . , 10-m), and forms a regenerated catalyst after charking.

Figure 2:
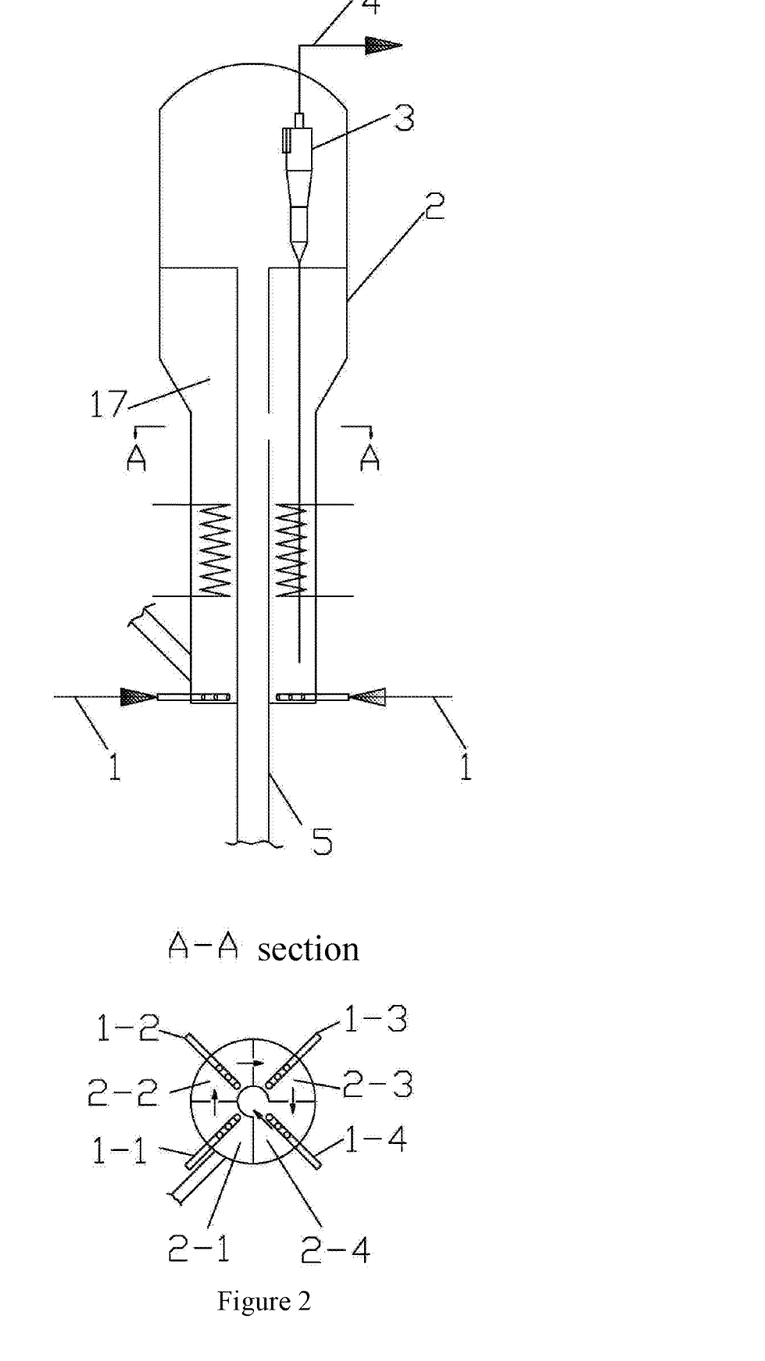
FIG. 2 is a structural schematic diagram of the dense phase fluidized bed comprising 4 secondary reaction zones in the present disclosure, wherein the arrows in the A-A sectional view show the flow direction of the catalyst between the secondary reaction zones.

In a more specific embodiment, the structural schematic diagram of the dense phase fluidized bed reactor comprising 4 secondary reaction zones in the present disclosure is as shown in FIG. 2. Three material flow controllers (17) and one baffle are vertically provided to separate the dense phase fluidized bed reaction zone into 4 secondary reaction zones. The catalyst is sequentially passed through the $1^{st}$ to the $4^{th}$ secondary reaction zones and is then passed into the stripper.

Figure 3:
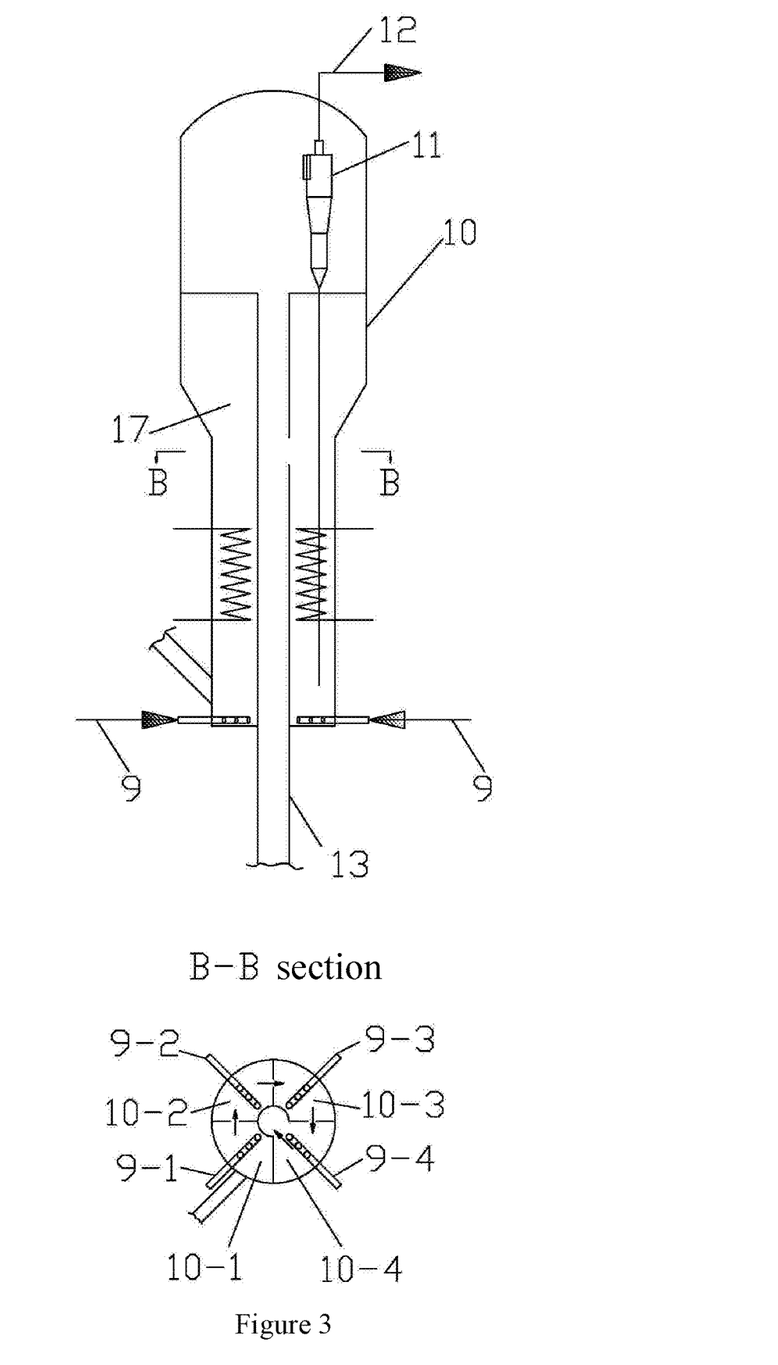
FIG. 3 is a structural schematic diagram of the dense phase fluidized bed comprising 4 secondary regeneration zones in the present disclosure, wherein the arrows in B-B sectional view show the flow direction of the catalyst between the secondary regeneration zones.

In a more specific embodiment, the structural schematic diagram of the dense phase fluidized bed regenerator comprising 4 secondary regeneration zones in the present disclosure is as shown in FIG. 3. Three material flow controllers (17) and one baffle are vertically provided to separate the regeneration zone into 4 secondary regeneration zones. The catalyst is sequentially passed through the $1^{st}$ to the $4^{th}$ secondary regeneration zones and is then passed into the stripper.

Figure 4:
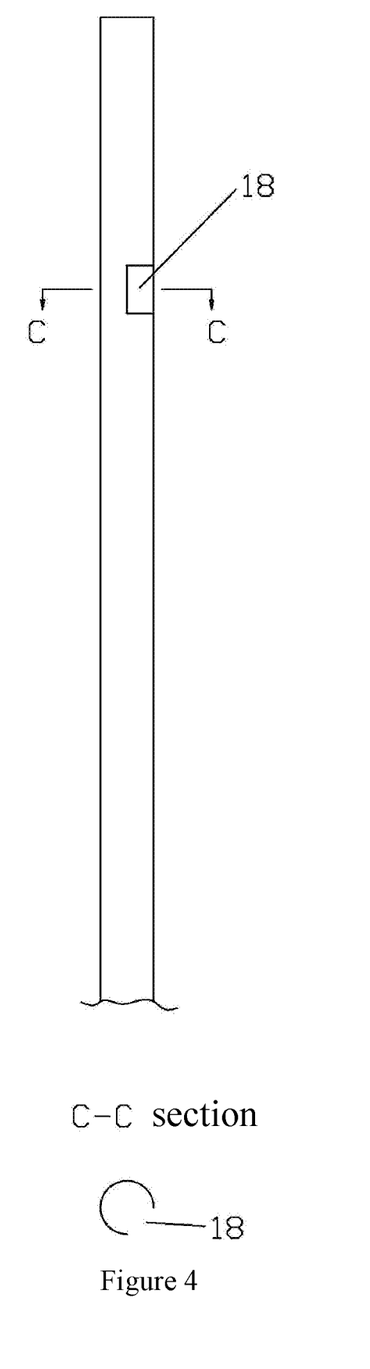
FIG. 4 is a structural schematic diagram of the stripper in the present disclosure.

In a more specific embodiment, the structural schematic diagram of the stripper in the present disclosure is as shown in FIG. 4. The opening on the tube wall on the upper part of the stripper is a material overflow port (18) between $n^{th}$ secondary reaction zone (or $m^{th}$ secondary regeneration zone) and the stripper.

Figure 5:
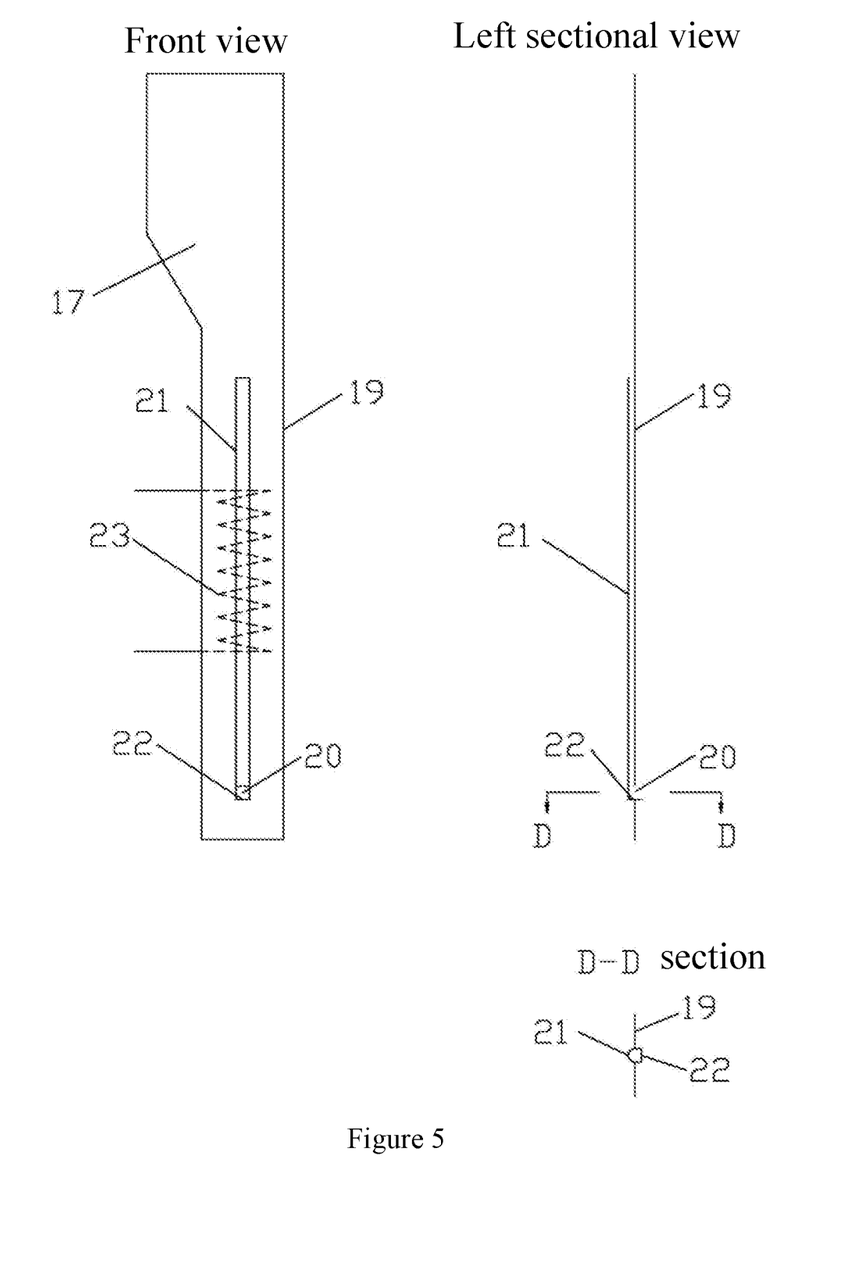
FIG. 5 is a structural schematic diagram of the material flow controller in the present disclosure.

In a more specific embodiment, the structural schematic diagram of the material flow controller in the present disclosure is as shown in FIG. 5. The material flow controller (17) is composed of a partition plate (19), an orifice (20), a material downward flow pipe (21), a bottom baffle (22) and a heat extraction member (23). The catalyst is passed into the material downward flow pipe from the top of the downward flow pipe, wherein the apparent linear velocity of gas is less than or equals to the minimal fluidizing velocity, the catalyst in the material downward flow pipe is in a dense phase packing state, and a material flow driving force is formed to drive the catalyst to flow into a next secondary reaction zone (or regeneration zone) via the orifice. A coil structure may be used as the heat extraction member, which is fixed onto the partition plate.

Preferably, in the above technical solutions, the apparent linear velocity of gas in the dense phase fluidized bed reaction zone is 0.1-1.5 m/s; the apparent linear velocity of gas in the dense phase fluidized bed regeneration zone is 0.1-1.5 m/s; the apparent linear velocity of gas in the material flow controller is less than or equals to the minimum fluidizing velocity of the catalyst; the catalyst includes SAPO-34 molecular sieve; a feed inlet is provided at the bottom of the reaction zone, and the feed includes methanol, dimethyl ether etc.; the stripping medium in the stripper includes water vapor; an inlet for regeneration medium is provided at the bottom of the regeneration zone, and the regeneration medium includes air, oxygen-deficient air, water vapor etc.; the reaction temperature in the reaction zone is 400-550° C., the bed density is 200-1200 kg/m$^3$, the average amount of carbon deposition on the catalyst increases sequentially from $1^{st}$ to $n^{th}$ secondary reaction zones, the average amount of carbon deposition in the $1^{st}$ secondary reaction zone is 0.5-3 wt %, the average amount of carbon deposition in the $n^{th}$ secondary reaction zone is 7-10 wt %; the reaction temperature in the regeneration zone is 500-700° C., the bed density is 200-1200 kg/m$^3$, the average amount of carbon deposition on the catalyst decreases sequentially from $1^{st}$ to $m^{th}$ secondary regeneration zones, the average amount of carbon deposition in the $1^{st}$ secondary regeneration zone is 3-10 wt %, and the average amount of carbon deposition in the $m^{th}$ secondary regeneration zone is 0-3 wt %. Using the method of the present disclosure, the object of controlling the amount of carbon deposition on catalyst, improving the uniformity of the carbon content and increasing the selectivity for light olefins can be achieved. Therefore, it has significant technical advantages, and is useful in the industrial production of light olefins.

For better illustrating the present disclosure, and facilitating the understanding of the technical solution of the present disclosure, the exemplary but non-limiting examples of the present disclosure are provided as follows.

Example 1

4 secondary reaction zones were provided in the dense phase fluidized bed reactor, and 4 secondary regeneration zones were provided in the dense phase fluidized bed regenerator. The raw material comprising an oxygen-containing compound was passed into the dense phase fluidized bed reactor and was brought into contact with a catalyst comprising SAPO-34 molecular sieve, to generate a gas phase product stream and a spent catalyst. The gas phase material and the entrained spent catalyst were passed into a cyclone separator. The gas phase product stream was passed into a subsequent separation section via an outlet of the cyclone separator, and the entrained spent catalyst was passed into $4^{th}$ secondary reaction zone via the dipleg of the cyclone separator. The regenerated catalyst was passed into the dense phase fluidized bed reactor through a stripper and a lift pipe, and sequentially passed through $1^{st}$ to $4^{th}$ secondary reaction zones, forming a spent catalyst after carbon deposition. The spent catalyst was further passed into the dense phase fluidized bed regenerator through a stripper and lift pipe, and sequentially passed through $1^{st}$ to $4^{th}$ secondary regeneration zones, forming a regenerated catalyst after charking. The reaction conditions in the dense phase fluidized bed reactor were as follows: the reaction temperature was 400° C., the linear velocity of gas was 0.3 m/s, the bed density was 1000 kg/m$^3$, the average amount of carbon deposition in the $1^{st}$ secondary reaction zone was 2 wt %, the average amount of carbon deposition in $2^{nd}$ secondary reaction zone was 6 wt %, the average amount of carbon deposition in $3^{rd}$ secondary reaction zone was 8 wt %, and the average amount of carbon deposition in $4^{th}$ secondary reaction zone was 10 wt %; the reaction conditions in the dense phase fluidized bed regenerator were as follows: the reaction temperature was 500° C., the linear velocity of gas was 0.3 m/s, the bed density was 1000 kg/m$^3$, the average amount of carbon deposition in $1^{st}$ secondary regeneration zone was 7 wt %, the average amount of carbon deposition in $2^{nd}$ secondary regeneration zone was 4 wt %, the average amount of carbon deposition in $3^{rd}$ secondary regeneration zone was 2 wt %, and the average amount of carbon deposition in $4^{th}$ secondary regeneration zone was 1 wt %. The reaction product was analyzed by on-line gas phase chromatography, and the carbon based yield of light olefins was 91.1 wt %.

Example 2

3 secondary reaction zones were provided in the dense phase fluidized bed reactor, and 2 secondary regeneration zones were provided in the dense phase fluidized bed regenerator. The raw material comprising an oxygen-containing compound was passed into the dense phase fluidized bed reactor and was brought into contact with a catalyst comprising SAPO-34 molecular sieve, to generate a gas phase product stream and a spent catalyst. The gas phase material and the entrained spent catalyst were passed into a cyclone separator, the gas phase product stream was passed into a subsequent separation section via an outlet of the cyclone separator, and the entrained spent catalyst was passed into $3^{rd}$ secondary reaction zone through the dipleg of the cyclone separator. The regenerated catalyst was passed into the dense phase fluidized bed reactor through a stripper and a lift pipe, and sequentially passed through $1^{st}$ to $3^{rd}$ secondary reaction zones, forming a spent catalyst after carbon deposition. The spent catalyst was passed into the dense phase fluidized bed regenerator through a stripper and lift pipe, and sequentially passed through $1^{st}$ to $2^{nd}$ secondary regeneration zone, forming a regenerated catalyst after charking. The reaction conditions in the dense phase fluidized bed reactor were as follows: the reaction temperature was 450° C., the linear velocity of gas was 0.5 m/s, the bed density was 900 kg/m$^3$, the average amount of carbon deposition in $1^{st}$ secondary reaction zone was 3 wt %, the average amount of carbon deposition in $2^{nd}$ secondary reaction zone was 7 wt %, and the average amount of carbon deposition in $3^{rd}$ secondary reaction zone was 9 wt %; the reaction conditions in the dense phase fluidized bed regenerator were as follows: the reaction temperature was 600° C., the linear velocity of gas was 0.7 m/s, the bed density was 700 kg/m$^3$, the average amount of carbon deposition in $1^{st}$ secondary regeneration zone was 4 wt %, and the average amount of carbon deposition in $2^{nd}$ secondary regeneration zone was 2 wt %. The reaction product was analyzed by on-line gas phase chromatography, and the carbon based yield of light olefins was 90.5 wt %.

Example 3

6 secondary reaction zones were provided in the dense phase fluidized bed reactor, and 5 secondary regeneration zones were provided in the dense phase fluidized bed regenerator. The raw material comprising an oxygen-containing compound was passed into the dense phase fluidized bed reactor, and was brought into contact with a catalyst comprising SAPO-34 molecular sieve, to generate a gas phase product stream and a spent catalyst. The gas phase material and the entrained spent catalyst were passed into a cyclone separator, the gas phase product stream was passed into a subsequent separation section via an outlet of the cyclone separator, and the entrained spent catalyst was passed into $6^{th}$ secondary reaction zone via the dipleg of the cyclone separator. The regenerated catalyst was passed into the dense phase fluidized bed reactor through a stripper and a lift pipe, and sequentially passed through $1^{st}$ to $6^{th}$ secondary reaction zones, forming a spent catalyst after carbon deposition. The spent catalyst was further passed into the dense phase fluidized bed regenerator through a stripper and a lift pipe, and sequentially passed through $1^{st}$ to $5^{th}$ secondary regeneration zones, forming a regenerated catalyst after charking. The reaction conditions in the dense phase fluidized bed reactor were as follows: the reaction temperature was 480° C., the linear velocity of gas was 0.7 m/s, the bed density was 700 kg/m$^3$, the average amount of carbon deposition in $1^{st}$ secondary reaction zone was 1 wt %, the average amount of carbon deposition in $2^{nd}$ secondary reaction zone was 3 wt %, the average amount of carbon deposition in $3^{rd}$ secondary reaction zone was 4 wt %, the average amount of carbon deposition in $4^{th}$ secondary reaction zone was 5 wt %, the average amount of carbon deposition in $5^{th}$ secondary reaction zone was 6 wt %, and the average amount of carbon deposition in $6^{th}$ secondary reaction zone was 7 wt %; the reaction conditions in the dense phase fluidized bed regenerator were as follows: the reaction temperature was 650° C., the linear velocity of gas was 1.0 m/s, the bed density was 500 kg/m$^3$, the average amount of carbon deposition in $1^{st}$ secondary regeneration zone was 5 wt %, the average amount of carbon deposition in $2^{nd}$ secondary regeneration zone was 3 wt %, the average amount of carbon deposition in $3^{rd}$ secondary regeneration zone was 2 wt %, the average amount of carbon deposition in $4^{th}$ secondary regeneration zone was 1 wt %, and the average amount of carbon deposition in $5^{th}$ secondary regeneration zone was 0.01 wt %. The reaction product was analyzed by on-line gas phase chromatography, and the carbon based yield of light olefins was 91.4 wt %.

The present invention has been described in detail above, but the invention is not limited to the specific embodiments described herein. It will be appreciated by those skilled in the art that other modifications and variations can be made without departing from the scope of the invention. The scope of the invention is defined by the appended claims.

What is claimed is:

1. A method for preparing a light olefin using an oxygen-containing compound, comprising the following steps:
   step a) in which a raw material comprising the oxygen-containing compound is introduced in parallel from n feeding branch lines into $1^{st}$ to $n^{th}$ secondary reaction zones in a dense phase fluidized bed reactor, and is brought into contact with a catalyst to generate a light olefin product-containing stream and a spent catalyst, wherein said catalyst is sequentially passed through $1^{st}$ to $n^{th}$ secondary reaction zones, with the carbon content thereof increasing gradually, and wherein said dense phase fluidized bed reactor is divided by a material flow controller into n secondary reaction zones;
   step b) in which the light olefin product-containing stream flowed out from the $1^{st}$ to $n^{th}$ secondary reaction zones is separated from the spent catalyst that it carries; said light olefin product-containing stream is passed into a product separation section, and after separation and purification, a light olefin product is obtained; the isolated spent catalyst is passed into the $n^{th}$ secondary reaction zone; and
   step c) in which the spent catalyst flowed out from the $n^{th}$ secondary reaction zone, after being stripped and lifted, is passed into a dense phase fluidized bed regenerator for regeneration; said spent catalyst is sequentially passed through $1^{st}$ to $m^{th}$ secondary regeneration zones; a regeneration medium is introduced in parallel from m feeding branch lines of regeneration zone into the $1^{st}$ to $m^{th}$ secondary regeneration zones; the spent catalyst is brought into contact with the regeneration medium, with the carbon content thereof decreasing gradually; after the completion of the regeneration, the catalyst is returned back to the $1^{st}$ secondary reaction zone via stripping and lifting; wherein the dense phase fluidized bed regenerator is divided by a material flow controller into m secondary regeneration zones;
   wherein n≥2 and m≥2.

2. The method according to claim 1, wherein 8≥n≥3 and 8≥m≥3.

3. The method according to claim 1, wherein, in the dense phase fluidized bed reactor, the apparent linear velocity of gas in the material flow controller is less than or equals to the minimum fluidizing velocity of the catalyst.

4. The method according to claim 1, wherein, in the dense phase fluidized bed regenerator, the apparent linear velocity of gas in the material flow controller is less than or equals to the minimum fluidizing velocity of the catalyst.

5. The method according to claim 1, wherein the catalyst comprises SAPO-34 molecular sieve.

6. The method according to claim 1, wherein the reaction conditions in the dense phase fluidized bed reaction zone are as follows: the apparent linear velocity of gas is 0.1-1.5 m/s, the reaction temperature is 400-550° C., and the bed density is 200-1200 kg/m$^3$.

7. The method according to claim 1, wherein the average carbon deposition amount of the catalyst is increased sequentially in the $1^{st}$ to $n^{th}$ secondary reaction zones of the dense phase fluidized bed, wherein the average carbon deposition amount of the catalyst in the $1^{st}$ secondary reaction zone is 0.5-3 wt %, and the average carbon deposition amount of the catalyst in the $n^{th}$ secondary reaction zone is 7-10 wt %.

8. The method according to claim 1, wherein the reaction conditions in the dense phase fluidized bed regeneration zone are as follows: the apparent linear velocity of gas is 0.1-1.5 m/s, the regeneration temperature is 500-700° C., and the bed density is 200-1200 kg/m$^3$.

9. The method according to claim 1, wherein the average carbon deposition amount of the catalyst is decreased sequentially from the $1^{st}$ to $m^{th}$ secondary regeneration zones of the dense phase fluidized bed regeneration zone, wherein the average carbon deposition amount of the catalyst in the $1^{st}$ secondary regeneration zone is 3-10 wt %, and the average carbon deposition amount of the catalyst in the $m^{th}$ secondary regeneration zone is 0-3 wt %.

10. The method according to claim 1, wherein the oxygen-containing compound is methanol and/or dimethyl ether; the light olefin is any one of ethylene, propylene or butylene, or a mixture thereof; and the regeneration medium is any one of air, oxygen-deficient air or water vapor, or a mixture thereof.

11. The method according to claim 1, said dense phase fluidized bed reactor comprising a reaction zone, a gas-solid separation zone, and a stripping zone, wherein the reaction zone is divided by a material flow controller into n secondary reaction zones, wherein n≥2.

12. The method according to claim 1, the dense phase fluidized bed regenerator comprising a regeneration zone, a gas-solid separation zone, and a stripping zone, wherein the regeneration zone is divided by a material flow controller into m secondary regeneration zones, wherein m≥2.

13. The method according to claim 11, wherein 8≥n≥3.

14. The method according to claim 11, wherein, in the dense phase fluidized bed reactor, the apparent linear velocity of gas in the material flow controller is less than or equals to the minimum fluidizing velocity of the catalyst.

15. The method according to claim 11, wherein the reaction conditions in the dense phase fluidized bed reaction zone are as follows: the apparent linear velocity of gas is 0.1-1.5 m/s, the reaction temperature is 400-550° C., and the bed density is 200-1200 kg/m$^3$.

16. The method according to claim 11, wherein the average carbon deposition amount of the catalyst is increased sequentially in the $1^{st}$ to $n^{th}$ secondary reaction zones of the dense phase fluidized bed, wherein the average carbon deposition amount of the catalyst in the $1^{st}$ secondary reaction zone is 0.5-3 wt %, and the average carbon deposition amount of the catalyst in the $n^{th}$ secondary reaction zone is 7-10 wt %.

17. The method according to claim 12, wherein 8≥m≥3.

18. The method according to claim 12, wherein, in the dense phase fluidized bed regenerator, the apparent linear velocity of gas in the material flow controller is less than or equals to the minimum fluidizing velocity of the catalyst.

19. The method according to claim 12, wherein the reaction conditions in the dense phase fluidized bed regeneration zone are as follows: the apparent linear velocity of gas is 0.1-1.5 m/s, the regeneration temperature is 500-700° C., and the bed density is 200-1200 kg/m$^3$.

20. The method according to claim 12, wherein the average carbon deposition amount of the catalyst is decreased sequentially from the $1^{st}$ to $m^{th}$ secondary regeneration zones of the dense phase fluidized bed regeneration zone, wherein the average carbon deposition amount of the catalyst in the $1^{st}$ secondary regeneration zone is 3-10 wt %, and the average carbon deposition amount of the catalyst in the $m^{th}$ secondary regeneration zone is 0-3 wt %.

* * * * *